(12) United States Patent
Hendriks et al.

(10) Patent No.: US 11,819,279 B2
(45) Date of Patent: Nov. 21, 2023

(54) PATIENT LUMEN SYSTEM MONITORING

(71) Applicant: KONINKLIJKE PHILIPS N.V., Eindhoven (NL)

(72) Inventors: Cornelis Petrus Hendriks, Eindhoven (NL); Valentina Lavezzo, Heeze (NL); Murtaza Bulut, Eindhoven (NL); Lieke Gertruda Elisabeth Cox, Eindhoven (NL); Hernán Guillermo Morales Varela, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 721 days.

(21) Appl. No.: 16/682,695

(22) Filed: Nov. 13, 2019

(65) Prior Publication Data
US 2020/0170711 A1 Jun. 4, 2020

(30) Foreign Application Priority Data
Nov. 30, 2018 (EP) .................................... 18290136

(51) Int. Cl.
*A61B 34/10* (2016.01)
*G16H 40/67* (2018.01)
(Continued)

(52) U.S. Cl.
CPC ............ *A61B 34/10* (2016.02); *A61B 5/0031* (2013.01); *A61B 5/14503* (2013.01);
(Continued)

(58) Field of Classification Search
CPC ..... A61B 5/02; A61B 5/02007; A61B 5/0031; A61B 5/08; A61B 5/14503; A61B 5/4842;
(Continued)

(56) References Cited

U.S. PATENT DOCUMENTS 9,984,465 B1 * 5/2018 Ma .......................... G16H 10/00
2002/0151816 A1 * 10/2002 Rich ................... A61B 5/02028
600/547

(Continued)

OTHER PUBLICATIONS

Charara, S., "Your doctor could soon be treating your virtual twin as a digital patient". https://www.wareable.com/health-and-wellbeing/doctor-virtual-twin-digital-patient-ucl-887. Retrieved from the Internet on Nov. 6, 2019.

(Continued)

*Primary Examiner* — Katrina R Fujita

(57) ABSTRACT

A computer system is disclosed comprising a processor arrangement communicatively coupled to a data storage arrangement storing a digital model of a section of a lumen system of a patient; and a communication module communicatively coupled to said processor arrangement and arranged to receive sensor data pertaining to an internal parameter of said lumen system from a sensor within said section of the lumen system. The processor arrangement is arranged to receive said sensor data from the communication module; retrieve said digital model from the data storage arrangement; simulate an actual physical condition of said lumen system by developing said digital model based on the received sensor data; and generate an output relating to said simulated actual physical condition for updating an electronic device. Also disclosed is a method of monitoring a patient with such a computer system, a computer program product for implementing such a method and a patient monitoring system.

19 Claims, 4 Drawing Sheets

(51) Int. Cl.
*G16H 10/60* (2018.01)
*G16H 50/50* (2018.01)
*A61B 5/00* (2006.01)
*A61B 5/145* (2006.01)
*G06T 17/00* (2006.01)

(52) U.S. Cl.
CPC ............. *G16H 10/60* (2018.01); *G16H 40/67* (2018.01); *G16H 50/50* (2018.01); *A61B 5/6862* (2013.01); *A61B 5/6876* (2013.01); *A61B 2034/105* (2016.02); *G06T 17/00* (2013.01); *G06T 2207/30101* (2013.01)

(58) Field of Classification Search
CPC ... A61B 5/6862; A61B 5/6876; A61B 5/7275; A61B 34/10; A61B 2034/105; G16H 10/60; G16H 40/67; G16H 50/50; G06T 17/00; G06T 2207/30101
See application file for complete search history.

(56) References Cited

U.S. PATENT DOCUMENTS

| | | | | |
|---|---|---|---|---|
| 2004/0242976 | A1* | 12/2004 | Abreu | A61B 5/746 600/315 |
| 2007/0055151 | A1* | 3/2007 | Shertukde | A61B 5/02007 600/437 |
| 2008/0020362 | A1* | 1/2008 | Cotin | G09B 23/285 434/267 |
| 2010/0121204 | A1* | 5/2010 | Utsuno | A61B 5/0285 600/506 |
| 2013/0197884 | A1 | 8/2013 | Mansi et al. | |
| 2015/0196229 | A1* | 7/2015 | Old | A61B 5/073 600/302 |
| 2016/0117819 | A1 | 4/2016 | Taylor | |
| 2017/0027649 | A1 | 2/2017 | Atilla et al. | |
| 2017/0286572 | A1 | 10/2017 | Hershey et al. | |
| 2018/0146926 | A1* | 5/2018 | Ishikawa | A61B 5/1495 |
| 2019/0005195 | A1* | 1/2019 | Peterson | G16H 50/20 |
| 2019/0005200 | A1* | 1/2019 | Zimmerman | G16H 50/30 |
| 2019/0087544 | A1* | 3/2019 | Peterson | G16H 50/20 |
| 2019/0198169 | A1* | 6/2019 | T | G16H 50/50 |
| 2019/0274528 | A1* | 9/2019 | Petroff | A61B 5/0084 |
| 2019/0342637 | A1* | 11/2019 | Halac | A61B 5/6847 |
| 2019/0355481 | A1* | 11/2019 | Lamb | G06N 3/006 |
| 2020/0105070 | A1* | 4/2020 | Coustaud | G06T 7/0012 |

OTHER PUBLICATIONS

Menichini, C. et al., "Predicting false lumen thrombosis in patient-specific models of aortic dissection". Journal of the Royal Society Interface Nov. 2016., 13 (124).

Neal, M.L. et al., "Current progress in patient-specific modeling", vol. II, No. 1. 111-126. 2010.

Nouri, M. et al., "Image-based computational simulation of sub-endothelial LDL accumulation in a human right coronary artery". Computers in Biology and Medicine 62(2015)206-221.

Aguado-Sierra, J. et al., "Patient-specific modeling of dyssynchronous heart failure: A case study". Progress in Biophysics and Molecular Biology 107 (2011) 147-155.

Mansi, T. et al., "Data-driven computational models of heart anatomy, mechanics and hemodynamics: A integrated framework". IEEE 2012.

Chen, X. et al., "Enabling Angioplasty-Ready "Smart" Stents to Detect In-Stent Restenosis and Occlusion". Advanced Science 2018, 5.

Takahata, K. et al., "Micromachined Antenna Stents and Cuffs for Monitoring Intraluminal Pressure and Flow". Journal of Microelectromechanical Systems, vol. 15, No. 5, Oct. 2006.

Gianchandani, Y.B.. "From Antenna Stents to Wireless Geiger Counters: The Promise of Electrical Micro-Discharges in the Fabrication and Operation of Microsensors". 2006 IEEE International Symposium on Micro-Nano Mechanical and Human Science, MHS. 1-6. 10.1109/MHS.2006.320302.

Fujinori, T. et al., "Development of Catheter Flow Sensor for Breathing Measurements at Different Levels of Tracheobronchial Airway". MDPI Proceedings 2017, 1, 356 (Eurosensors Paris 2017).

Liu, B. et al. "Influence of model boundary conditions on blood flow patterns in a patient specific stenotic right coronary artery". BioMedical Engineering OnLine 2015, 14(Suppl 1):S6.

Shishir, S. et al., "Blood Flow Dynamics in Cerebral Aneurysm—A CFD Simulation". Procedia Engineering 105 (2015) 919-927.

Yu, X. et al. "Computational fluid dynamics analysis on recurrence of simple coiling intracranial aneurysms with remnant neck". Chinese Neurosurgical Journal (2016) 2:30.

* cited by examiner

PATIENT LUMEN SYSTEM MONITORING

FIELD OF THE INVENTION

The present invention relates to a computer system comprising a processor arrangement communicatively coupled to a data storage arrangement storing a digital model of a section of a lumen system of a patient.

The present invention further relates to a method of monitoring a physical condition of a lumen system of a patient with such a computer system.

The present invention further relates to a computer program product for implementing such a method with such a computer system.

The present invention further relates to a patient monitoring system comprising such a computer program product or computer system.

BACKGROUND OF THE INVENTION

In many developed countries, the provision of healthcare is becoming increasingly strained. Some reasons for this include the growth of the population and increasing life expectancy. Unfortunately, although people live longer, the average age at which their health deteriorates to the point where regular medical care is required is not increasing accordingly, such that the ageing population is unwell for longer, which increases the pressure on the healthcare system, e.g. on medical practitioners, medical infrastructures such as hospitals, diagnostic equipment therein, and so on. Hence, rather than simply increasing medical resources, for which the financial resources may not be available, there exists a need to improve the efficiency of such healthcare systems.

A recent development in artificial intelligence (AI) is the so-called digital twin concept. In this concept, a digital representation (the digital twin) of a physical system is provided and connected to its physical counterpart, for example through the Internet of things as explained in US 2017/286572 A1 for example. Through this connection, the digital twin typically receives data pertaining to the state of the physical system, such as sensor readings or the like, based on which the digital twin can predict the actual status of the physical system, e.g. through simulation.

Such digital twin technology is becoming of interest in the medical field, as it provides an approach to more efficient medical care provision. For example, the digital twin may be built using imaging data of the patient, e.g. a patient suffering from a diagnosed medical condition as captured in the imaging data, as for instance is explained by Dr Vanessa Diaz in https://www.wareable.com/health-and-wellbeing/doctor-virtual-twin-digital-patient-ucl-887 as retrieved from the Internet on 29 Oct. 2018. Such a digital twin may serve a number of purposes.

One application domain is the prediction of the development of abnormalities in a lumen system of the patient, such as the patient's cardiovascular system. For example, Claudia Menichini et al., in Journal of the Royal Society Interface, 2016 Nov. 13(124) discloses a computational model that is capable of predicting thrombus formation, growth and its effects on blood flow under physiological conditions. Predictions of thrombus formation and growth are based on fluid shear rate, residence time and platelet distribution, which are evaluated through convection-diffusion-reaction transport equations. The model is applied to a patient-specific type B dissection for which multiple follow-up scans are available. It was found that the predicted thrombus formation and growth patterns were in good qualitative agreement with clinical data, demonstrating the potential applicability of the model in predicting false lumen (FL) thrombosis for individual patients.

Such a computational model typically is a static model in the sense that it has been constructed using imaging data captured at a single point in time. However, many potentially serious changes to a patient's health cannot be predicted using such a static model, for example because such changes are the direct result of changes to the lumen system. In such a scenario, the model may be updated by more up to date imaging data, but this requires the patient to visit a healthcare facility, which may be inconvenient to the patient and increases the work pressure of the healthcare facility. However, it is not straightforward to avoid such subsequent imaging to update the digital twin of the patient, in particular where the changes to the patient's lumen system are not signalled by indicators that can be captured external to the patient's body.

SUMMARY OF THE INVENTION

The present invention seeks to provide a computer system that can accurately predict changes to a physical state of a section of a patient's lumen system without the need for updated imaging data.

The present invention further seeks to provide a method of monitoring a physical condition of a lumen system of a patient with such a computer system.

The present invention further seeks to provide a computer program product for implementing such a method with such a computer system.

The present invention further seeks to provide a patient monitoring system comprising such a computer program product or computer system.

According to an aspect, there is provided a computer system comprising a processor arrangement communicatively coupled to a data storage arrangement storing a digital model of a section of a lumen system of a patient; and a communication module communicatively coupled to said processor arrangement and arranged to receive sensor data pertaining to an internal parameter of said lumen system from a sensor within said section of the lumen system, wherein the processor arrangement is arranged to receive said sensor data from the communication module, retrieve said digital model from the data storage arrangement, simulate an actual physical condition of said lumen system by developing said digital model based on the received sensor data; and generate an output relating to said simulated actual physical condition for updating an electronic device.

The present invention is based on the insight that changes to a section of a lumen system of a patient, such as a patient's cardiovascular system or a pulmonary system, e.g. an arterial or bronchial system, can be monitored using a sensor within the patient, e.g. an implanted sensor, an ingested sensor or the like, in which the sensor is arranged to update a boundary condition of the actual physical state simulated with the digital model of the patient, i.e. the patient's digital twin. In this manner, a change in the physical condition of the lumen system may be detected from within the patient's body using his or her digital twin, as the sensor data produced by the internal sensor, e.g. a pressure sensor or flow sensor, can be leveraged by the digital twin to predict changes to the state of the patient's lumen system by development of the digital model using the sensor data. This for example allows the digital model to predict anomalies in the patient's lumen system in locations other than the location of the internal sensor, which anomaly in the absence of the deployment of such a digital model would be difficult to detect with a sensor, as it would require the positioning of the sensor in close vicinity to the location of the anomaly within the patient's lumen system, which location is near-impossible to predict prior to the occurrence of the anomaly. This is because the digital model typically implements a computational model that calculates a parameter field or parameter distribution pattern in a computational anatomical domain, such as a lumen model. Such a lumen model typically comprises borders such as fluid inlets and fluid outlets, which each may be associated with specified boundary conditions, i.e. parameter values or distributions. Because of the interrelation between the parameter values of distributions across the computational anatomical domain, a determined parameter value in a specific location of the patient's anatomy that is modelled by the computational anatomical domain, e.g. a parameter value obtained with an implanted sensor, parameter values may be predicted in other locations within the computational anatomical domain based on the relationship between these parameter values as captured in the computational model.

In order to develop the digital model, the processor arrangement may deploy a fluid dynamics model, a systemic model or a fluid-structure interaction model depending on the type of lumen system that is being monitored.

In an embodiment, the electronic device is a data storage device comprising an electronic medical record of the patient, in which the output produced by the processor arrangement is configured to update the medical record with the simulated actual physical condition of the lumen system of the patient. This for instance may be used to keep the electronic medical record of the patient up to date, such that a medical practitioner may remotely monitor a medical condition of the patient by consulting the electronic medical record, thereby reducing the need to meet with the patient in person.

In another embodiment, the processor arrangement is arranged to generate said output upon establishing a relevant difference between the simulated actual physical condition and a previously simulated physical condition of said lumen system. This for instance may be used to only update the aforementioned electronic medical record when a change in a medical condition of the patient, i.e. a change in the physical state of the lumen system of the patient, is detected, in order to limit the size of such a medical record.

Furthermore, such conditional generation of the output may be used in other ways. As an example embodiment, the electronic device may be the sensor within said section of the lumen system, in which the output is configured to change a mode of operation of said sensor. The output for instance may trigger the increase of a sampling frequency of the sensor if the simulated actual physical state of the lumen system of the patient indicates an increase in the likelihood of the occurrence of an anomaly therein, in which case a higher sampling frequency of the sensor data may be warranted to provide more intensive monitoring of the patient's lumen system in order to reduce the risk of such an anomaly occurring or causing a significant deterioration in the patient's health.

As another example embodiment, the electronic device may be a mobile communication device registered to the patient, and wherein said output is configured to generate a message on said mobile communication device. Such a message for example may alert the patient to make an appointment with the relevant medical practitioner or may inform the patient of the details of an automatically scheduled appointment for instance.

The processor arrangement further may be arranged to generate said digital model from image information of said section of the lumen system, such as for example a digital arterial model from one or more angiograms of the patient.

According to another aspect, there is provided a method of monitoring a physical condition of a lumen system of a patient with a computer system comprising a processor arrangement communicatively coupled to a data storage arrangement storing a digital model of a section of a lumen system of a patient; and a communication module communicatively coupled to said processor arrangement and arranged to receive sensor data pertaining to an internal parameter of said lumen system from a sensor within said section of the lumen system, the method comprising, with said processor arrangement, receiving said sensor data from the communication module, retrieving said digital model from the data storage arrangement; simulating an actual physical condition of said lumen system by developing said digital model based on the received sensor data; and generating an output relating to said simulated actual physical condition for updating an electronic device. With such a computer-implemented method, the physical state of a lumen system of a patient may be accurately monitored using a sensor within the lumen system and a digital model or digital twin of the patient modelling a section of the lumen system, thereby obviating or at least reducing the need for the patient to visit a medical professional in person to obtain an up to date state of the patient's lumen system.

To this end, the development of the digital model may be based on the received sensor data comprises using a fluid dynamics model, a systemic model or a fluid-structure interaction model in order to obtain the simulated actual physical state of the lumen system of the patient.

In an embodiment, generating said output is conditional upon establishing a relevant difference between the simulated actual physical condition and a previously simulated physical condition of said lumen system, e.g. a difference indicating a clinical change in the physical condition of the lumen system. This for example may be used to control a mode of operation of the sensor with the produced output or to generate an electronic message on a mobile communication device of the patient, e.g. to inform the patient of the need to make an appointment with the relevant medical practitioner or to inform the patient of such an appointment having been made automatically.

The method may further comprise generating said digital model from image information of said section of the lumen system with the processor arrangement.

According to another aspect, there is provided a computer program product for a computer system comprising a processor arrangement communicatively coupled to a data storage arrangement storing a digital model of a section of a lumen system of a patient and a communication module communicatively coupled to said processor arrangement and arranged to receive sensor data pertaining to an internal parameter of said lumen system from a sensor within said section of the lumen system, the computer program product comprising a computer readable storage medium having computer readable program instructions embodied therewith for, when executed on the processor arrangement, cause the processor arrangement to implement the method of any of the herein described embodiments. Such a computer program product for instance may be used to configure existing computer systems to implement the method according to embodiments of the present invention.

According to another aspect, there is provided a patient monitoring system comprising the computer program product or a computer system according to any of the herein described embodiments and the sensor for generating the sensor data pertaining to an internal parameter of said lumen system from within said section of the lumen system. With such a patient monitoring system, the need for the patient to visit a medical professional in person to obtain an up to date state of the patient's lumen system is obviated or at least reduced when the sensor is within the lumen system of the patient such that the actual physical state of the patient's lumen system may be simulated using the digital model thereof.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
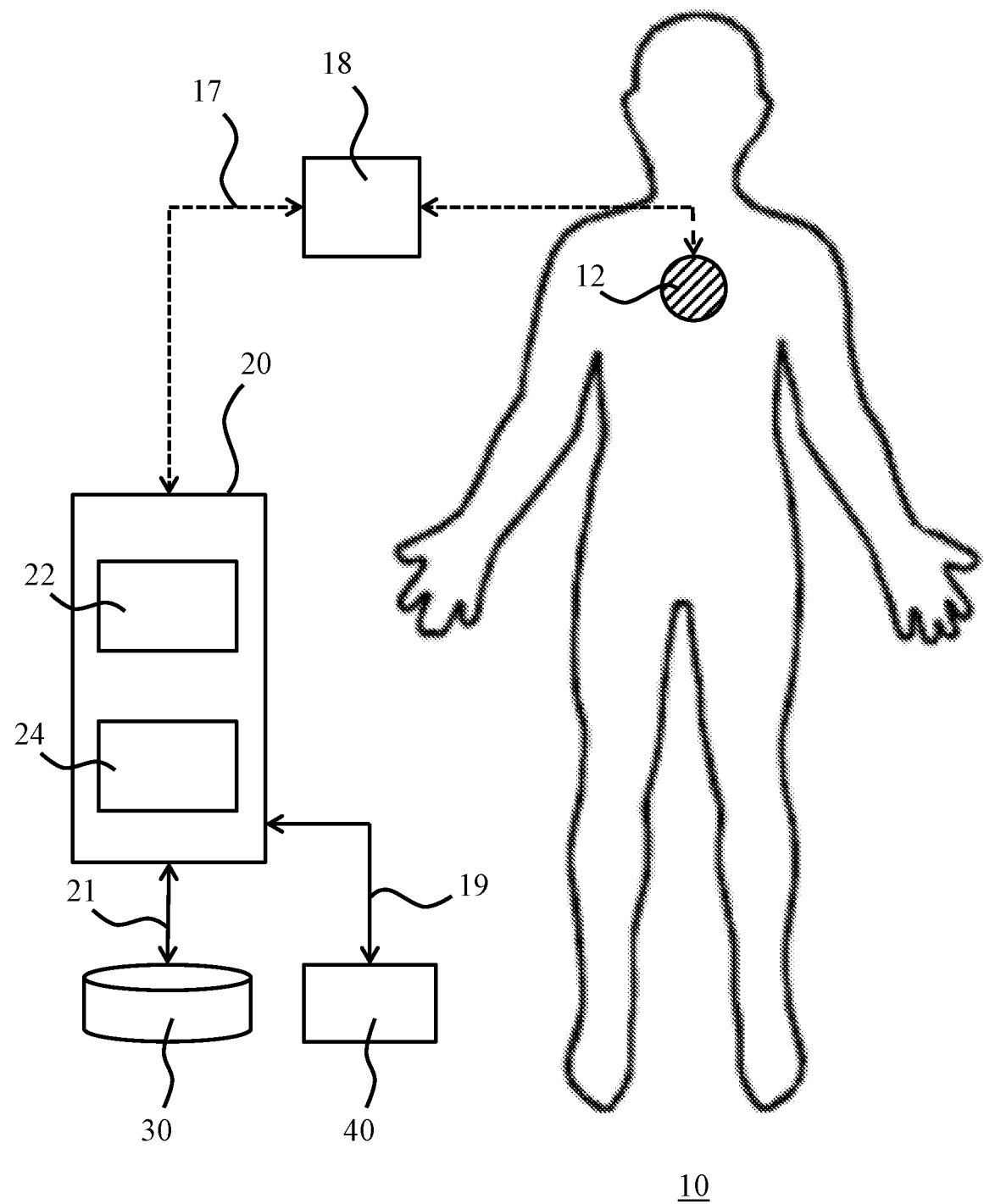
FIG. 1 schematically depicts a patient monitoring system according to example embodiments.

It should be understood that the Figures are merely schematic and are not drawn to scale. It should also be understood that the same reference numerals are used throughout the Figures to indicate the same or similar parts.

Figure 2:
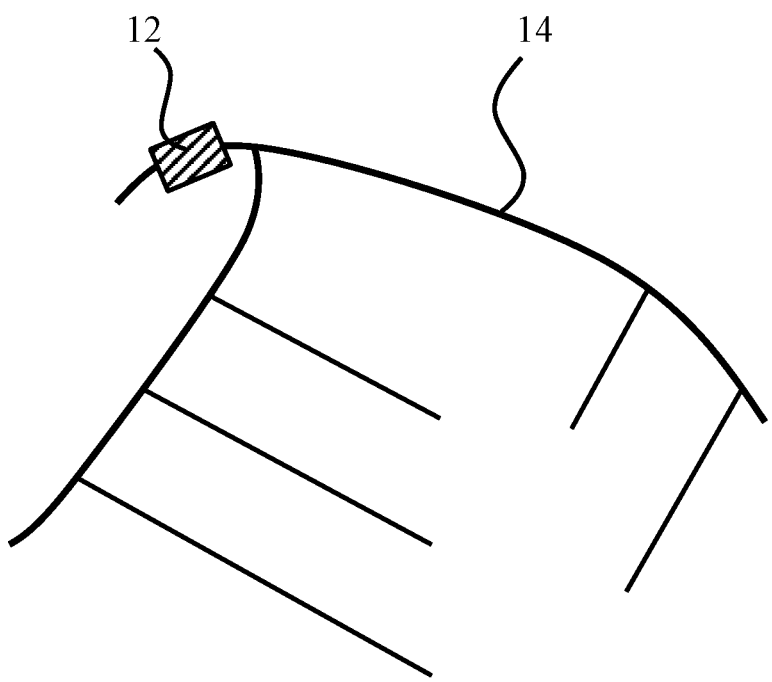
FIG. 2 schematically depicts a section of a lumen system of a patient.

FIG. 1 schematically depicts a generalised setup to which embodiments of the present invention are applicable. A lumen system 14 of a patient 10, e.g. part of the cardiovascular system or pulmonary system of the patient as schematically depicted in FIG. 2, is monitored by at least one sensor 12 within the lumen system arranged to provide sensor data to a computer system 20 comprising a processor arrangement 22 and a data communication module 24 to which the one or more sensors are communicatively coupled through a data link 17. The sensor 12 typically is wirelessly connected to a control module 18 when in communication range with the sensor 12, which control module 18 is communicatively coupled to the computer system 20 for relaying the sensor data received from the sensor 12 to the computer system 20.

Such a sensor 12 may monitor a fluid parameter of a fluid flowing through the lumen system, e.g. as a pressure sensor or flow sensor, which data as will be explained in further detail below by means of a number of example use cases may be used to derive a (general) physical state of the lumen system therefrom with a digital representation of the lumen system of the patient hosted on the computer system 20. Such a sensor 12 may be an implantable sensor, such as for example a stent or coil equipped with one or more pressure or flow sensors, for example to detect heart failure or in-stent restenosis, or more generally for local blood flow monitoring, e.g. to monitor aneurysms or stent patency by way of non-limiting example. It is noted that the sensor 12 may be implanted into the patient 10 without the need for surgical procedures, e.g. through inhalation or swallowing.

The processor arrangement 22 of the computer system 20 may take any suitable shape. In the context of the present invention, a processor arrangement may comprise one or more processors, processor cores and the like that cooperate to form such a processor arrangement. Similarly, the data communication module 24 may take any suitable shape, such as a wireless or wired data communication module, as is well known in the art and will therefore not be further explained for the sake of brevity only.

The data link 17 may take any suitable shape, such as a wireless communication link, a wired communication link or a combination thereof. Any suitable communication protocol may be deployed between the one or more sensors and the communication module 24 over the data link 17. For example, in case of a wireless communication link, the communication protocol may be Wi-Fi, Bluetooth, a mobile phone communication protocol such as 3G, 4G, 5G and so on. Other examples of suitable wireless communication links will be immediately apparent to the skilled person. In case of a wired communication link, suitable application protocols may include TCP/IP and similar protocols used to communicate over a wired data communication link such as a wired network, e.g. the Internet.

The computer system 20 is typically remote from the patient 10 such that the patient 10 may be monitored from a distance. For example, the computer system 20 may comprise a remote server or the like on which the digital twin of the patient 10 is hosted, from which a medical professional in charge of remotely monitoring the patient 10 may intervene based on simulation results provided with the digital twin. Alternatively, such intervention may be performed by the computer system 20 itself, e.g. by scheduling an appointment for the patient 10 to see the medical professional in person and informing the patient 10 of the appointment details.

The computer system 20 may be communicatively coupled over a data link 21 to a data storage arrangement 30, which may store a digital model of the physical entity 10. In the context of the present application, the data storage arrangement 30 may comprise any suitable number of data storage devices, which may be accessible to the computer system 20 over one or more data links 21. Any suitable type of data storage arrangement 30 may be used for this purpose, such as a data storage device forming part of the computer system 20, or a data storage device 30 that is accessible by the computer system 20 over a network such as a storage area network (SAN) device, a network attached storage (NAS) device, a cloud storage device, and so on.

The digital model in the remainder of this application will also be referred to as a digital twin of the patient 10. Such a digital twin typically provides a model of both the elements and the dynamics of how the patient 10 (i.e. the physical twin) operates and lives throughout his or her life cycle. To this end, the digital twin may comprise a definition of the connection between the patient 10 and the digital twin, which connection is established by generating real time data using the one or more sensors 12 within the lumen system of the patient 10. Such a digital twin may integrate artificial intelligence, machine learning and software analytics with spatial network graphs to create a 'living' digital simulation model of the patient 10. Specifically, where the digital twin comprises a model of part of a lumen system of the patient 10, such a living digital simulation may involve the use of a fluid dynamics model, a systemic model or a fluid-structure interaction model in order to develop the digital twin based on the sensor data provided by the one or more sensors 12 within the lumen system of the patient 10.

In other words, the sensor data provided by the one or more sensors 12 within the lumen system of the patient 10 to the computer system 20 hosting the digital twin through its processor arrangement 22 is used to update and change the digital twin such that any changes to the patient 10 as highlighted by the sensor data are reflected in the digital twin. As such, the digital twin forms a learning system that learns from itself using the sensor data provided by the one or more sensors 12.

Optionally, the digital twin may further consider user information pertaining to the patient 10, e.g. symptoms or the like. To this end, the computer system 20 may be communicatively coupled to a user interface 40, which may provide such user information to the computer system 20 over a data communication link 19. The user interface 40 may form part of an electronic device registered to the patient 10, for example a smart phone, tablet computer, desktop computer and so on. Alternatively, the user interface 40 may form part of the computer system 20, e.g. in the form of a peripheral device connected to the computer system 20 using a communication port or the like, such that a medical practitioner may provide such user information to the digital twin.

The biophysical model, i.e. the digital twin, of the patient 10 may be developed from patient data, e.g. imaging data such as CT images, MRI images, ultrasound images, and so on. A typical workflow for creating and validating a 3D, subject-specific biophysical model is depicted in "Current progress in patient-specific modeling", by Neal and Kerckhoff, 1, 2009, Vol. 2, pp. 111-126. For example, in case of a digital twin representing part of the cardiovascular system of the patient 10, such a biophysical model may be derived from one or more angiograms of the patient. In an embodiment, the sensor data produced by the sensor 12 is used to continuously or periodically update the boundary condition of a flow simulation through the digital lumen model (i.e. the digital twin) of the patient 10. As previously explained, the boundary condition of such a flow simulation may comprise an estimation of a parameter value or distribution of parameter values at a boundary of the lumen model, such as a lumen inlet or outlet. This estimation may be achieved via assumption, calculation, or preferably a measurement with a sensor 12 implanted in a specific location within the patient 10, which specific location is mimicked in the digital twin as will be understood from the foregoing.

For example, a boundary condition of the lumen model such as an inlet parameter may be measured in the physical domain with an implanted sensor 12. From this measurement, parameters inside the whole domain of the lumen model can be calculated using a predefined interrelationship between such parameter values. In this manner, potential problems, e.g. a low wall shear stress in case of the lumen model modelling a blood vessel, can be derived from the calculated parameters throughout this whole domain, that is, away from the location of the implanted sensor 12. Hence, the implantation of such a sensor within a section of the lumen system of the patient 10 facilitates the monitoring of the entire section of this lumen using the digital model, thereby obviating the need for such a sensor 12 to be in close vicinity to an anomaly in the lumen system of the patient 10, as the anomaly may be predicted using the aforementioned parameter interrelations and lumen model boundary conditions.

Figure 3:
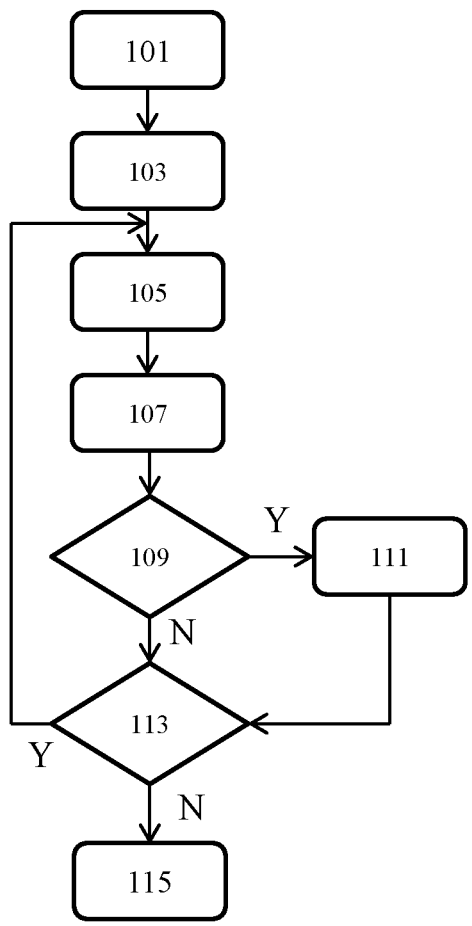
FIG. 3 is a flowchart of a patient monitoring method according to an embodiment.

FIG. 3 is a flowchart of a generalized method of operating monitoring a physical condition of a lumen system 14 of a patient 10 with the computer system 20 according to an example embodiment. The method 100 commences in operation 101 after which the method 100 proceeds to operation 103 in which the digital representation (i.e. the digital twin) of the patient 10 is loaded onto the computer system 20, e.g. by retrieving the digital twin from the data storage arrangement 30. Next, in operation 105 the computer system 20 receives the sensor data from the sensor(s) 12 within the lumen system 14 of the patient 10 over the data communication link 17, which sensor data as previously explained represents monitored pressure or flow parameters within the lumen system 14 of the patient 10, as will be explained by way of non-limiting example with a number of use cases below. Operation 105 may further comprise receiving user information pertaining to a physical state of the patient 10 by the computer system 20 through a user interface 40 as explained in further detail above.

In operation 107 of the method 100, the processor arrangement 22 develops the digital twin using the received sensor data in order to simulate the actual physical state of the lumen system 14 of the patient 10. This may be actual sensor data or may include historical sensor data, e.g. to model the development of an anomaly over time, such as wall shear stress parameter data over a period of time to model plaque growth within the lumen system over this period. In operation 109 the processor arrangement 22 checks whether the actual physical state of the lumen system 14 of the patient 10 has relevantly changed, for example by comparing the simulated actual physical state of the lumen system 14 of the patient 10 against previously simulated or otherwise determined physical states of the lumen system 14 of the patient 10 to establish a (clinically) relevant difference between the actual and previous physical states of the lumen system 14. This difference is compared against a threshold to determine whether the change in the previously determined physical state is (clinically) relevant. Alternatively, such a threshold may define a boundary value of a safety window in which the parameter monitored with the sensor(s) 12 should lie, such that exceeding such a threshold is indicative of the patient 10 being in or approaching an unsafe physical state, e.g. developing a serious health condition.

If no significant change in the monitored physical state of the lumen system 14 of the patient 10 is detected, the method 100 may directly proceed to operation 113 in which the processor arrangement 22 determines if the monitoring of the lumen system 14 of the patient 10 is to be continued, e.g. on the basis of a user input to this effect received through a user interface such as the user interface 40. If this is the case, the method 100 reverts back to operation 105; otherwise, the method 100 terminates in operation 100.

On the other hand, if a significant change in the monitored physical state of the lumen system 14 of the patient 10 is detected in operation 109, the method 100 may cause the processor arrangement 22 to generate on or more outputs in operation 111. For example, the processor arrangement 22 may generate an output in the form of a control signal for the sensor(s) 12 and provides this control signal to the controller 18 of the appropriate sensor 12 through the data communication link 17, e.g. using the data communication module 24. The control signal triggers the controller 18 to change the mode of operation of the sensor 12, such as for example a sampling frequency of that sensor. In this manner, battery life of the sensor(s) 12 can be preserved as long as the lumen system 14 of the patient 10 is in a state of equilibrium, or at least exhibits only (clinically) insignificant changes to its physical state as indicated by the sensor data produced by the sensor(s) 12 by initially operating the sensor(s) 12 at a low sampling frequency.

The justification of this approach is that the likelihood of sudden catastrophic changes to a stable lumen system 14 of the patient 10 is negligible, such that a low sampling rate or frequency of such a sensor may be deployed without running the risk of a physical condition of the patient 10 becoming unstable during a period in which the sensor is idle. However, this risk can no longer be considered negligible once the digital twin simulation indicates that the lumen system 14 of the patient 10 is no longer in a state of equilibrium as indicated by a (clinically) relevant in its physical state as previously explained, as in such a scenario the risk of such catastrophic changes has increased. In such a scenario, it is therefore desirable to increase the sampling frequency of the sensor in order to more frequently monitor further changes to the physical state of the lumen system 14 of the patient 10, e.g. in order to more accurately prevent undesired changes in the physical state of the lumen system 14 of the patient 10 from occurring.

Additionally or alternatively, the processor arrangement 22 may in operation 111 produce an output in the form of an electronic message to an electronic device such as a mobile communication device registered to the patient 10. In such a scenario, the output typically is configured to generate a message on the mobile communication device, e.g. on its user interface 40, in which case the message may be sent over the data communication link 19. Such a message for example may alert the patient 10 to the need to schedule a medical appointment or procedure to manage his or her medical condition, for example to prevent escalation of the medical condition to becoming potentially life-threatening or debilitating. Alternatively, the computer system 20 may automatically schedule such an appointment, e.g. by consultation of an electronic diary of the relevant medical practitioner, in which case the message may inform the patient 10 of the details of this appointment. Many variations to such an electronic message will be immediately apparent to the skilled person.

Figure 4:
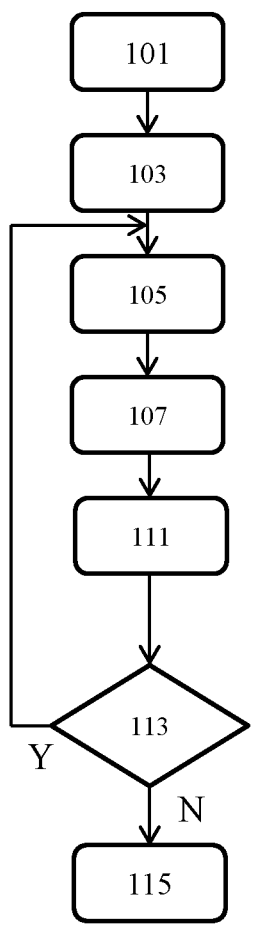
FIG. 4 is a flowchart of a patient monitoring method according to another embodiment.

In addition, the processor arrangement 22 may update an electronic medical record of the patient 10, e.g. an electronic medical record stored on the data storage arrangement 30, with the simulation results of the simulated actual physical state of the lumen system 14 of the patient. This enables a medical practitioner to remotely monitor a medical condition of the patient 10, such that the patient 10 may be scheduled for a consultation in person only when the simulation results obtained with his or her digital twin give cause for such a consultation, thereby avoiding the need for periodic face to face checks of the patient 10. In an alternative embodiment of the method 100 as depicted by the flowchart in FIG. 4, the comparison operation 109 may be omitted, such that the output produced by the processor arrangement 22 in operation 111 simply may be the update of such an electronic medical record of the patient 10.

Embodiments of the present invention may be advantageously deployed in the monitoring of patients that have undergone a medical procedure or suffer from a medical condition involving fluid flow (e.g. blood flow or air flow) through a lumen system of the patient 10, such as an arterial or bronchial system. Non-limiting examples of suitable applications of the present invention include Coronary Artery Bypass Grafting (CABG), Transcatheter Aortic Valve Implantation (TAVI), aneurysms, mitral annuloplasty, lung disease monitoring (e.g. COPD), urinary diseases monitored with an implantable bladder sensor, glaucoma (intra-ocular pressure IOP), intracranial pressure monitoring, intra-abdominal pressure monitoring (oedema, pneumothorax) and heart failure management. In such examples, a sensor within the relevant lumen system 14, e.g. an implanted sensor in combination with a biophysical model of the lumen system 14 may be used to accurately monitor the progress of such medical conditions and/or the general condition (physical state) of the lumen system 14 of a patient 10 having undergone such a procedure or suffering from such a medical condition.

The teachings of the present invention will now be explained in further detail by way of the following non-limiting examples.

A first example embodiment is concerned with the monitoring of low wall shear stress in the coronary arteries of a patient 10. Low wall shear stress in the coronary arteries is associated with sub-endothelial lipid accumulation and atherosclerosis risk (plaque formation). Low wall shear stress is accessible to calculation using computational fluid dynamics, as reported by M. Nouri et al., in Computers in Biology and Medicine, 62 (2015) pages 206-221. However, the pressure and velocity boundary conditions that are imposed in computational models have considerable impact on flow velocity and shear stress predictions. Therefore, accuracy of in vivo measurements of blood pressure and velocity is of great importance for reliable model predictions.

Coronary interventions such as bypass grafting or percutaneous coronary intervention (PCI) offer an opportunity to place a sensor 12 in the coronary arterial tree. Patients undergoing this procedure are at high risk in terms of medical health, and follow-up monitoring of the hemodynamics in the coronary arterial tree can help to prevent re-occurrence, for instance by providing an early warning in the case of deterioration. The sensor 12 can be integrated in a stent which is used to treat the problem, or a in a dedicated sensor device which is positioned remotely from the stent or bypass, for instance up- or downstream.

After the medical procedure, a patient specific computational model (the digital twin of the lumen system 14) is constructed. The geometry of the arterial tree is determined from an angiogram which is already available from the medical intervention. A computational method such as for example computational fluid dynamics, a systemic model, or a fluid-structure interaction model, is applied to simulate the flow pattern in the arterial tree. The boundary conditions for the simulations are obtained from the sensor data, and are updated on a regular basis, e.g. continuously or intermittently such as periodically. For example, when the physiological condition of the patient is relatively stable, i.e. the sensor data is indicative of constant parameter values, intermittent measurements can be taken at pre-determined time intervals, e.g. daily, weekly, monthly. When the patient 10 is deteriorating as expressed by run-out parameter values captured by the sensor 12, or is in an acute condition (ED, ICU), it can be decided by the processor arrangement 22 to start measuring continuously with the sensor 12, causing the processor arrangement 22 to generate the sensor control signal in operation 111 as previously explained.

The processor arrangement 22 may run the simulation using the digital twin of the patient 10 continuously or intermittently, e.g. periodically, depending on the requirements. From the simulation results, low wall shear stress patterns and relevant metrics are derived, for example the number of locations with a low wall shear stress below a critical value, such as for example a location with a low wall shear stress of less than 10% of the mean low wall shear stress. This for example may be derived from the flow field through the lumen model at every location therein. Machine learning techniques such as regression analysis may be deployed to predict risk levels based on simulated low wall shear stress patterns, provided that enough training data are available. This information can be stored in the electronic medical record of the patient 10 as previously explained and be used in a planned follow-up risk assessment, as an alternative for, or complementary to, routine angiography. Alternatively, in case a routine follow-up is not yet planned, the processor arrangement 22 may generate the message for the mobile communication device registered to the patient 10 in order to warn the patient to consult a physician.

A second example embodiment is concerned with the risk assessment of cerebral aneurysms. Catheter angiography is commonly used in the follow-up of brain aneurysms which have been minimally invasively treated with coils or stents. The catheter is used in case an additional intervention is needed in this follow-up, e.g. to insert additional coils or another stent. In many cases, such additional intervention is unnecessary as found during such follow-up procedures. Such unnecessary additional interventions expose the patient 10 to unnecessary health risks. A biophysical model of the relevant section of the arterial system of the patient 10 and an implanted sensor 12, e.g. integral to a stent or coil placed during the initial procedure can reduce the number of invasive procedures that does not lead to an intervention, i.e. the placement of an additional stent or coil. Instead, invasive follow-up procedures only use a catheter in the follow-up procedure if the digital twin provides an indication to do so.

For this purpose, a simulation such as a computational flow dynamics simulation is carried out based on the information from an angiogram of the relevant section of the arterial system of the patient, and the sensor data from the sensor 12 within this system, such as flow or pressure data. The biophysical model geometry (i.e. the digital twin) comprises the remnant aneurysm sac and the parent artery. The sensor data provides a boundary condition for the computational flow dynamics simulation. From the computational flow dynamics simulation, for example the low wall shear stress is determined, which is a known critical parameter for rupture risk of the aneurysm. Based on the simulated trends in the low wall shear stress, decisions can be made on whether or not, or how to intervene.

A third example embodiment involves the monitoring of patients having a high risk of suffering a serious problem with a lumen system. In the previous example embodiments, the placement of an implantable sensor 12 was performed in the context of a planned intervention related to an already diagnosed problem which needed to be treated. Alternatively, the placement of such an implantable sensor 12 may also be performed in the case of a high risk patient 10 in need of monitoring only. In this case, the sensor 12 may be inserted in a minimally invasive way such as by using a needle, a small incision, catheterization, swallowing or inhaling, for example. The sensor data provided by the sensor 12 device subsequently may be complemented with the biophysics model (i.e. the digital twin). Any of the previously mentioned non-limiting examples of suitable applications of the present invention may benefit from this embodiment.

A fourth example embodiment is concerned with the monitoring of lung function. Lung air flow obstruction is commonly measured with an external flow device such as a spirometer, for example to diagnose chronic obstructive pulmonary disease (COPD). However, this method does not provide local information on lesions and on the development of lesions. Lesions may exist and develop without being detected by spirometry. Sometimes catheters are used to assess local flow or collateral ventilation between lobes, for example to plan interventions such as (endobronchial-) lung volume reduction (LVR).

In this embodiment, a patient specific flow model is used to simulate the lung function of the patient (FEV1, FVC) as an alternative for, or complementary to, spirometry. To this end, the patient 10 may be implanted with an flow sensor 12 for longitudinal monitoring of COPD. Such sensors are well-known per se and are therefore not explained in further detail for the sake of brevity only. The data from the implanted flow sensors provide the boundary conditions for the computational flow dynamics simulations. As an example, the simulated lung function can be used to help predicting upcoming exacerbations, e.g. using algorithms based on subjective and objective data. Compared to a lung function measured using spirometry, this has the advantage that the simulated lung function provides an extra objective measure on a continuous basis, and the simulated lung function is not dependent on how a user handles the spirometer, which often leads to inaccurate data.

The above described embodiments of the method 100 executed by the processor arrangement 22 may be realized by computer readable program instructions embodied on a computer readable storage medium having, when executed on a processor arrangement 22 of a computer system 20, cause the processor arrangement 22 to implement any embodiment of the method 100. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the computer system 20 is adapted to retrieve the computer readable program instructions from such a computer readable storage medium and to create a new computer readable storage medium by storing the retrieved computer readable program instructions in a data storage arrangement 30 accessible to the computer system 20, e.g. in a memory device or the like forming part of the computer system 20.

Furthermore, any suitable sensor 12 as described above may be combined with such a computer program product, or with a computer system 20 on which the computer program product is installed, to provide a patient monitoring system for monitoring a physical condition of a lumen system 14 of a patient by implanting the sensor 12 in this lumen system and monitoring the boundary conditions of such a lumen system 14 with the digital twin of this lumen system based on the sensor data provided by the sensor 12 when in situ.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A computer system comprising:
a processor arrangement communicatively coupled to a data storage arrangement storing a digital model of a section of a lumen system of a patient; and
a communication module communicatively coupled to said processor arrangement and arranged to receive sensor data pertaining to an internal parameter of said lumen system from a sensor within said patient in said section of the lumen system, and wherein the sensor is an implanted sensor or an ingested sensor;
wherein the processor arrangement is arranged to:
receive said sensor data from the communication module;
retrieve said digital model from the data storage arrangement;
simulate an actual physical condition of said lumen system by developing said digital model based on the received sensor data; and
generate an output relating to said simulated actual physical condition for updating an electronic device, wherein said output is configured to change a mode of operation of said sensor between a first mode having a first sampling frequency and a second mode having a different second frequency, wherein the change of mode of operation is done in response to said simulated actual physical condition alternating between a stable lumen system and an unstable lumen system.

2. The computer system of claim 1, wherein the lumen system is a cardiovascular system or a pulmonary system.

3. The computer system of claim 1, wherein the processor arrangement is arranged to develop said digital model based on the received sensor data using a systemic model or a fluid-structure interaction model.

4. The computer system of claim 1, wherein the processor arrangement is arranged to generate said output upon establishing a relevant difference between the simulated actual physical condition and a previously simulated physical condition of said lumen system.

5. The computer system of claim 4, wherein said electronic device is the sensor within said section of the lumen system.

6. The computer system of claim 4, wherein said electronic device is a mobile communication device registered to the patient, and wherein said output is configured to generate a message on said mobile communication device.

7. The computer system of claim 1, wherein said electronic device is a data storage device comprising a medical record of the patient, and wherein said output is configured to update said medical record with the simulated actual physical condition of the lumen system of the patient.

8. The computer system of claim 1, wherein the processor arrangement further is arranged to generate said digital model from image information of said section of the lumen system.

9. The computer system of claim 1, wherein the sensor is integral to a stent or a coil.

10. The computer system of claim 1, wherein the sensor is the ingested sensor.

11. A method of monitoring a physical condition of a lumen system of a patient with a computer system comprising:

a processor arrangement communicatively coupled to a data storage arrangement storing a digital model of a section of a lumen system of a patient; and
a communication module communicatively coupled to said processor arrangement and arranged to receive sensor data pertaining to an internal parameter of said lumen system from a sensor within said patient in said section of the lumen system, and wherein the sensor is an implanted sensor or an ingested sensor;
the method comprising, with said processor arrangement:
receiving said sensor data from the communication module;
retrieving said digital model from the data storage arrangement;
simulating an actual physical condition of said lumen system by developing said digital model based on the received sensor data; and
generating an output relating to said simulated actual physical condition for updating an electronic device, wherein said output is configured to change a mode of operation of said sensor between a first mode having a first sampling frequency and a second mode having a different second frequency, wherein the change of mode of operation is done in response to said simulated actual physical condition alternating between a stable lumen system and an unstable lumen system.

12. The method of claim 11, wherein developing said digital model based on the received sensor data comprises using a systemic model or a fluid-structure interaction model for said development.

13. The method of claim 11, wherein generating said output is conditional upon establishing a relevant difference between the simulated actual physical condition and a previously simulated physical condition of said lumen system.

14. The method of claim 11, further comprising, with said processor arrangement, generating said digital model from image information of said section of the lumen system.

15. The method of claim 11, wherein the lumen system is a cardiovascular system or a pulmonary system.

16. A computer program product for a computer system comprising a processor arrangement communicatively coupled to a data storage arrangement storing a digital model of a section of a lumen system of a patient; and a communication module communicatively coupled to said processor arrangement and arranged to receive sensor data pertaining to an internal parameter of said lumen system from a sensor within said section of the lumen system;
the computer program product comprising a non-transitory computer readable storage medium having computer readable program instructions embodied therewith for, when executed on the processor arrangement, cause the processor arrangement to implement the method of claim 11.

17. A patient monitoring system comprising the computer program product of claim 16 or a computer system and the sensor for generating the sensor data pertaining to an internal parameter of said lumen system from within said section of the lumen system.

18. The method of claim 11, wherein the sensor is integral to a stent or a coil.

19. The method of claim 11, wherein the sensor is the ingested sensor.

* * * * *